United States Patent [19]

Yannas et al.

[11] Patent Number: 4,505,266
[45] Date of Patent: Mar. 19, 1985

[54] METHOD OF USING A FIBROUS LATTICE

[75] Inventors: Ioannis V. Yannas, Newton Center; John F. Burke, Belmont, both of Mass.

[73] Assignee: Massachusetts Institute of Technology, Cambridge, Mass.

[21] Appl. No.: 601,233

[22] Filed: Apr. 17, 1984

Related U.S. Application Data

[62] Division of Ser. No. 315,233, Oct. 26, 1981, Pat. No. 4,458,678.

[51] Int. Cl.$^3$ ............................................. A61B 19/00
[52] U.S. Cl. ........................................ 128/1 R; 428/2
[58] Field of Search .................. 128/1 R, 155–156; 427/2; 3/1; 604/890–900, 266; 424/34, 35, 94, 31, 32

[56] References Cited

U.S. PATENT DOCUMENTS

| | | | |
|---|---|---|---|
| 3,800,792 | 4/1974 | McKnight et al. | 128/DIG. 8 |
| 3,826,678 | 7/1974 | Hoffman et al. | 3/1 |
| 3,955,012 | 5/1976 | Okamura et al. | 3/1 |
| 4,304,866 | 12/1981 | Green et al. | 128/1 R |
| 4,326,532 | 4/1982 | Hammer | 604/266 |
| 4,352,883 | 10/1982 | Lim | 3/1 |

OTHER PUBLICATIONS

I. V. Yannas et al., "Permanent Closure of Deep Wounds with a Polymeric Membrane", Abstract of Presentation, Internat. Union of Pure and Appl. Chem., Strasbourg, France, Internat'l. Symp. on Macromolecules, Jul. 6–9, 1981.
I. V. Yannas et al., "Prompt Long-Term Functional Replacement of Skin", American Society for Artificial Organs, vol. 27 (1981).
I. V. Yannas et al., "Artificial Skin Design: Permanent Closure of Full Thickness Skin Wounds", Proc. 1st World Biomatenal Congr., B. D. Winter (ed.), Wiley, New York, (1981).
Yannas et al., "Design of an Artificial Skin II Control of Chemical Composition," J. Biomed. Mat. Res. 14:107–132 (1980).

Primary Examiner—John D. Yasko
Assistant Examiner—Harrie Stein Samaras
Attorney, Agent, or Firm—Arthur A. Smith, Jr.; David E. Brook

[57] ABSTRACT

This invention relates to the introduction of viable cells into a fibrous lattice by surgical, force-utilizing, or other manipulative techniques, all of which are referred to herein as "seeding." One embodiment comprises an autografting technique which involves intact tissue. Other embodiments which involve the distribution of an aqueous suspension of cells comprise centrifugal, spraying, pipetting and syringe emplacement. Each cell that survives the seeding process may reproduce into a colony of cells which grow until they reach confluence, thereby creating a uniform layer or volume of tissue. By proper placement of cells capable of generating such colonies, the period of recovery of a wound may be drastically reduced. In addition, research by the Applicants indicates that tissue that is regenerated using the methods of this invention to seed a lattice comprising collagen and glycosaminoglycan tends to be smoother, more uniform, less fibrotic, less scarred and more flexible than tissue that is regenerated by wound contraction or conventional autografting.

5 Claims, 5 Drawing Figures

METHOD OF USING A FIBROUS LATTICE

DESCRIPTION

The invention described herein was supported in whole or in part by grants from the National Institutes of Health.

This application is a division of application Ser. No. 315,233, filed 10-26-81 now U.S. Pat. No. 4,458,678.

TECHNICAL FIELDS

This invention is in the fields of medicine, surgery, biology, biochemistry, and polymers.

BACKGROUND ART

Damage to or loss of the skin can be a very serious injury, resulting in extreme pain, disfigurement, mutilation, and frequently death. Medical and surgical treatment of severely burned people is very time-consuming and expensive, and requires elaborate equipment and highly-trained personnel. Extensive scarring and wound contracture can lead to physiological, emotional and societal impairment.

Skin loss or injury is most commonly caused by fire or scalding, by mechanical or chemical injury, or by skin lesions. Since burns are the most common cause of skin injury, burn injury is referred to herein; however it should be understood that, with possible minor exceptions known to those who are skilled in the art, the treatment of skin loss or damage caused by any type of injury or disease may be conducted according to the methods of this invention.

A person or animal that suffers from a burn, injury, disease, or removal of all or a portion of the skin or an organ is referred to herein as a "patient." An area of the body where tissue has been lost, damaged, diseased, or surgically removed is referred to herein as a "wound" or a "woundbed." An area of intact skin or organ from which cells are harvested, or a cell bank or tissue culture from which cells are harvested or otherwise taken, is referred to herein as a "donor site." Tissue that is regenerated by cell growth upon a wound is referred to herein as "neodermal," "neoepidermal," or "neo-organ" tissue.

SKIN STRUCTURE

Normal, undamaged skin is composed of several layers [1]. A simplified representation of a segment of intact skin is shown in FIG. 1. The outer layer, usually called the epidermis, is composed of several types of epithelial cells. It contains nerve fibrils, but not blood vessels. The outermost layer of epidermis, usually called the *stratum corneum*, comprises squamous (i.e., relatively flat) cells that typically have low rates of reproduction; these cells are gradually sloughed off by abrasion, and are replaced by cells from the lower layers. The next lower layer is usually called the *stratum lucidum*, which may be absent in certain areas. The lowest layer of squamous cells is usually called the *stratum granulosum*. Below it are two layers of nonsquamous cells: the *stratum malpighii* (also called the *rete mucosum*) and the *stratum germinativum*.

Cells that are at or near the base of the epidermis (near the dermis) are often called basal cells. These have relatively high rates of reproduction, and may give rise to other basal cells, or to maturing epidermal cells which do not subsequently reproduce. Epidermal cells produce keratin, a protein which may be secreted or contained in cell walls. This protein is relatively hard, and imparts toughness and strength to the skin.

Below the epidermis is a layer of cells and connective tissue called the dermis. This layer comprises mesenchymal cells, which includes fibroblast cells and cells of blood and lymph vessels. Hair follicles, sebaceous glands, and sweat glands extend from the dermis to the surface of the skin; such glands and follicles are lined by epithelial cells.

Mesenchymal cells produce and secrete collagen, a fibrous protein. Such collagen forms a structural matrix that surrounds and contains the cells, which increases the strength of the tissue.

The interface between the dermis and epidermis is folded and papillary, rather than flat or level. Therefore, a burn that is relatively level may remove all of the epidermis and part of the dermis at numerous locations, while leaving clusters of intact epidermal cells interspersed in the damaged area. A burn that is somewhat deeper may remove all of the surface layers of epidermal cells (and some dermal cells as well), without destroying the epithelial cells that line hair follicles and sebaceous and sweat glands. If this occurs, the epithelial cells from the follicles and glands may proliferate and migrate over the wound, creating a shallow layer of epidermis. Such a layer is often irregular and thin, and it may impede proper healing of the wound. Either of the burns discussed above is classified as a second degree burn. A burn that destroys the epidermis and the full thickness of the dermis, including the epithelial cells that line follicles and glands, is classified as a "full thickness" or third degree burn [2].

BURN TREATMENT

A patient who has suffered extensive skin loss or injury is immediately threatened by infection and by excessive loss of fluids. To meet both of these needs, a severe skin wound must be closed promptly by some type of membrane. A variety of attempts have been made to meet this need. References to papyrus or animal skin date back to about 1500 B.C. Specially prepared pigskin is often used by surgeons today because of its ready commercial availability. These xenografts (i.e., membranes of non-human origin) can cover a wound for about three to five days. However, they are rejected by the patient, leaving behind an open wound. Therefore, they must usually be removed or changed after a few days, and serve essentially as a stopgap while the patient's skin slowly heals [3].

Homografts, also called allografts, can be obtained from human cadavers. However, they are in short supply and, like xenografts, are commonly rejected after a brief period. Immunosuppressive drugs may be used to delay or reduce the rejection of xenografts or homografts, thereby extending the period that they may cover a woundbed. However, the use of immunosuppressive drugs increases the vulnerability of the patient to infection [4].

Autografts are partial-thickness sections of skin which are removed ("harvested") from an undamaged area of the patient or possibly from the patient's identical twin, and transplanted onto a wounded area. Unlike xenografts or homografts, autografts are not rejected by the patient; instead, they become permanently attached to the wound and proliferate, thereby providing a new layer of epidermis and dermis which closes the wound [5].

The harvesting operation is usually performed with an instrument called a dermatome, which contains an oscillating blade and adjusting devices that control the depth and the width of the cut [6]. Since cells in the *stratum corneum* normally do not reproduce rapidly, virtually all harvesting operations remove cells from the *stratum granulosum*. Because of the papillary nature of skin, most harvesting operations also remove cells from the *stratum malpighii* and the *stratum germinativum*, as well as significant amounts of dermis.

The harvesting operation is a painful, invasive process, which causes scarring. It should therefore be kept to a minimum. In addition, a badly injured patient may suffer skin loss or damage on nearly all of his or her body. This may severely limit the amount of healthy, intact skin that is available for autografting. When this occurs, xenografts or homografts may be placed across the entire wound surface to control infection and dehydration; they are gradually replaced as autografts become available. Autografts may be harvested repeatedly from a donor site. In such an operation, an area of xenograft or homograft is removed and discarded, and replaced by an autograft. Each donor site must be allowed to heal before another autograft is removed from it; this requires a substantial delay, and prolongs the recovery of the patient.

In one important modification of the autografting process, a pattern of slits is cut into a piece of harvested skin. This allows the skin to be stretched into a mesh, thereby increasing the wound area that can be covered by that piece of skin [7]. After grafting, the autologous cells migrate and proliferate, closing up the gaps caused by the slits. Eventually, with the aid of autografts, the entire wound area is covered by a layer of replaced skin which is subject to various problems such as hypertrophic scarring, discomfort, and disabling contracture.

THE BILAYER MEMBRANE

The Applicants are co-inventors (along with certain other persons) of a synthetic multilayer membrane (herein referred to as a bilayer membrane) that is useful in treating skin loss or injury. See U.S. Pat. Nos. 4,060,081 (Yannas et al, 1977) and 4,280,954 (Yannas et al, 1981), the teachings of which are hereby incorporated by reference. Briefly, the top layer of this membrane comprises a polymer such as a silicone elastomer. This layer imparts several desired physical properties to the membrane, including tensile strength, suturability, control of moisture flux, and impermeability to bacteria and viruses. The bottom layer comprises a highly porous lattice made of collagen and glycosaminoglycan (GAG), also referred to as mucopolysaccharide. Various forms of GAG which may be suitable for use in this material include chondroitin 6-sulfate, chondroitin 4-sulfate, heparin, heparan sulfate, keratan sulfate, dermatan sulfate, chitin, and chitosan.

The collagen/GAG lattice effectively serves as a supporting or "scaffolding" structure in or on which epithelial and mesenchymal cells from the burn victim can grow and proliferate. Its composition and structure are controlled so that it does not provoke a substantial immune response by the graft recipient, and it is slowly biodegraded into non-toxic substances that are utilized or eliminated by the body.

It is possible to control several parameters (primarily crosslinking density, porosity and GAG content) of the collagen/GAG lattice to control the rate at which the lattice is biodegraded by collagenase and other enzymes. Lattices that are biodegraded too quickly will disappear before sufficient healing occurs, while lattices that are biodegraded too slowly tend to impede cell migration and to cause the formation of a fibrotic layer of cells surrounding the lattice. It is believed that a lattice that is biodegraded after about thirty days is preferable for use on burn patients.

When a burn patient is admitted to a hospital, areas of skin that have been entirely destroyed or severely damaged often contain dead or damaged skin, called "eschar." The eschar usually is surgically removed to prevent it from interfering with the healing process. The entire area of damaged and dead skin is excised, so that intact epithelial cells are present at the perimeter of the wound. The bilayer membrane discussed above is carefully draped across the wound surface to avoid the entrapment of air pockets between the wound and the membrane. The membrane normally is sutured to the intact skin using conventional techniques. The grafted area is then covered with a bandage.

The collagen/GAG lattice has been observed by the Applicants to reduce wound contraction. In general, wound contraction comprises horizontal motion by existing cells in, and the periphery of, the wound. It results in substantial distortion and scarring, so its prevention or reduction is very desirable.

Within a period of several days, healthy cells from the woundbed begin to migrate into and proliferate within the collagen/GAG lattice of the membrane. Mesenchymal cells and minute blood vessels migrate in a direction that is perpendicular to the plane of the membrane, as shown in FIG. 2. Since the skin surface is regarded herein as horizontal, the direction of mesenchymal cell growth is referred to herein as vertical. Epithelial cells migrate across the surface of the lattice in a horizontal direction (i.e., along the plane of the membrane). Since burns and other skin wounds tend to be relatively shallow, mesenchymal cells need not migrate very far in order to create a neodermis. However, epithelial cells may be required to migrate great distances to create a neoepidermis and close the wound.

Within thirty days, epithelial cells are capable of migrating and proliferating horizontally a distance of about 0.75 cm. Therefore, a wound with a horizontal minor dimension no larger than about 1.5 cm could be closed by epithelial migration within about thirty days, assuming that epithelial cells are closing the wound from all sides. However, extensive burns often exceed 1.5 cm in every direction. For example, it is not unusual for a badly burned patient to lose virtually all of the skin below the shoulders. Therefore, epithelial cells cannot reach the interior areas of a large wound by normal migration for periods exceeding hundreds of days. When used with very large wounds, a collagen/GAG lattice with a biodegradation rate of about 30 days would be entirely biodegraded long before the epithelial cells could close the wound.

DISCLOSURE OF THE INVENTION

This invention relates to the introduction of cells into a fibrous lattice in order to promote the growth of cells or the generation of tissue at a wound. The introduction of cells according to this invention is done by surgical, force-utilizing or other manipulative techniques, all of which are referred to herein as "seeding." Seeding is distinct from the spontaneous infiltration, migration and reproduction of cells which occur when a biocompatible lattice is placed adjacent to the perimeter of a wound. One type of fibrous lattice that is suitable for seeding by the methods of this invention comprises collagen that is crosslinked with glycosaminoglycan.

Cells can be introduced by the methods of this invention into any specific desired location in a fibrous lattice, and they can be uniformly distributed over any desired area of a fibrous lattice. Each cell that survives the seeding process may reproduce and multiply into a colony of cells. Separate colonies in a lattice may grow until they reach confluence, thereby creating a uniform layer or volume of regenerated neodermal, neoepidermal, or neo-organ tissue. By proper placement of cells capable of generating such colonies, the period of recovery may be drastically reduced. In addition, tissue that is regenerated using the methods of this invention to seed a collagen/glycosaminoglycan lattice tends to be smoother, more uniform, less fibrotic, less scarred and more flexible than tissue that is regenerated by normal wound contraction or conventional autografting.

BEST MODES OF CARRYING OUT THE INVENTION

Numerous preferred embodiments are available for seeding cells into porous collagen lattices. Several such embodiments are described herein. Various subheadings are provided below for convenience, and are not intended to describe or limit the embodiments discussed thereunder.

Each embodiment has certain advantages and disadvantages, and is therefore likely to be particularly appropriate for one or more specific types of wounds or treatment objectives. In addition, each embodiment may be used in conjunction with other embodiments to provide a multifaceted, flexible treatment program that may be modified during the course of treatment to respond to a patient's condition and progress of recovery.

AUTOGRAFTING

Figure 3:
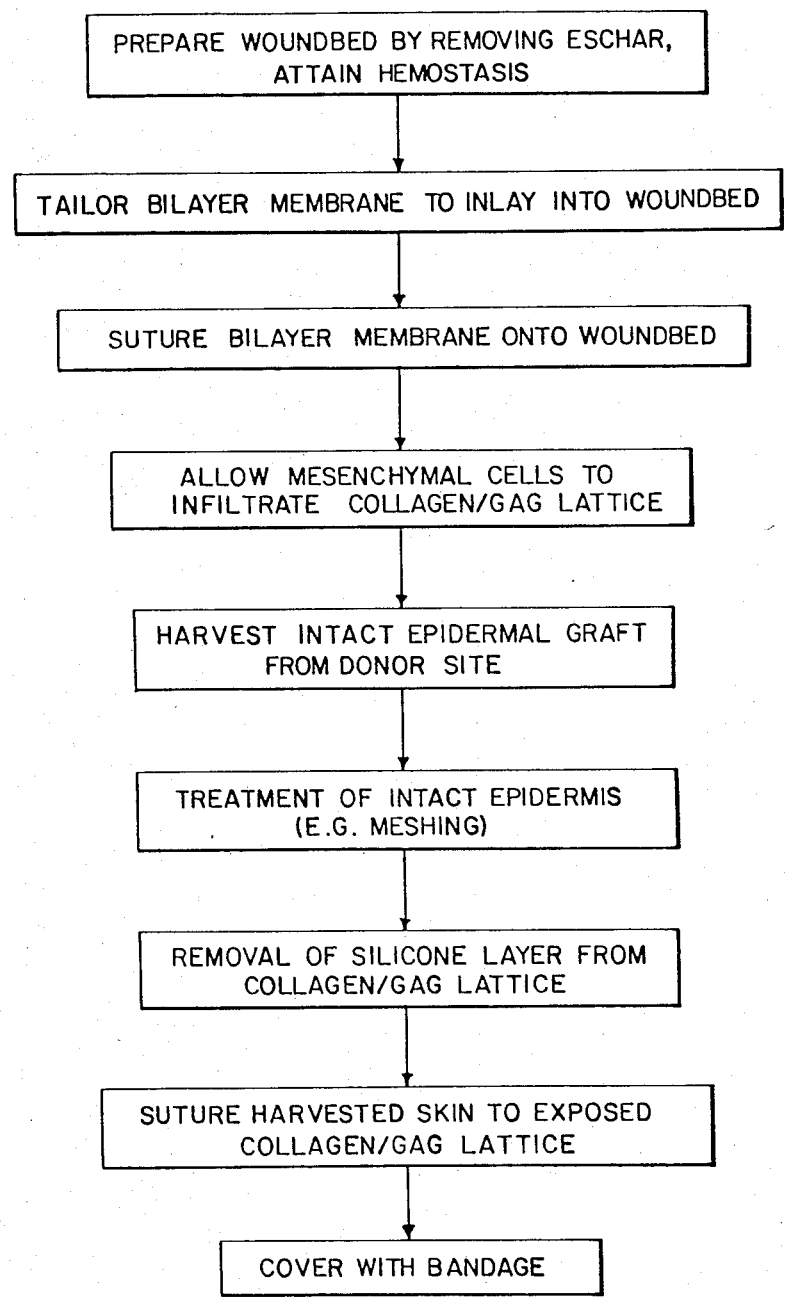
FIG. 3 is a flow chart indicating a sequence of steps comprising an autografting embodiment according to this invention.

One preferred embodiment of this invention involves the use of the bilayer membrane in a manner that somewhat resembles, but is distinct from, autografting techniques involving xenografts of allografts. As described previously, one layer of this membrane comprises a collagen/GAG lattice, and the other layer comprises a silicone rubber moisture transmission control layer. The sequence of steps involved in the autografting embodiment is displayed as a flow chart in FIG. 3.

In this embodiment, the woundbed is prepared, if necessary, by surgically removing eschar or otherwise damaged skin. A piece of unseeded membrane is trimmed, if necessary, by scissors or scalpel to an appropriate size, and carefully draped across the wound. Efficient contact and displacement of air pockets can be achieved if the flexural rigidity of the membrane is sufficiently low; this can be achieved by proper manipulation of certain parameters during the manufacture of the membrane. The membrane is initially held in place by sutures. Since the surface energy of the wound-membrane interface is less than the surface energy of a wound-air interface, the membrane maintains efficient contact with the wound during the process of infiltration by cells and blood vessels. The rate of infiltration depends upon several factors, including the depth of the wound, the type and condition of cells exposed in the woundbed, and the porosity, thickness, and GAG content of the membrane.

Under the current state of the art, the growth of epithelial cells in vivo or in vitro is believed to be promoted by the presence of fibroblast, endothelial and other mesenchymal cells [8]. To exploit this phenomenon, the autoepidermalgrafting procedure of this embodiment may be delayed for a period of several days to weeks, until a sufficient number of mesenchymal cells and blood vessels have grown into the membrane to promote the growth of epithelial cells, or until sufficient intact cells are available for harvesting from a donor site.

When this stage is reached, the patient is anesthetized and a thin layer of epidermis containing epithelial cells (and possibly mesenchymal cells) is harvested from a donor site by using a dermatome or other cutting device. The piece of epidermis may be treated by meshing to expand its area, using conventional techniques. An appropriately sized piece of the silicone layer is removed from the collagen/GAG membrane that was previously grafted onto the patient. Silicone removal may be accomplished by making an incision at the periphery of the area to be autografted, and carefully peeling the silicone off of the underlying collagen/GAG lattice, without removing or detaching the lattice from the woundbed. The harvested piece of epidermis is then placed on top of the exposed collagen lattice, and sutured in place. Any covering or bandage that has appropriate rates of moisture flux or absorption is thereafter placed over the autografted area to help prevent infection and dehydration.

The cells within the autografted piece of epidermis migrate and reproduce until they grow to confluence, thereby regenerating neoepidermis. The collagen lattice is eventually biodegraded, and is replaced by new collagen which is created by the cells growing within the lattice. The bandage is removed after the neoepidermis has closed the wound.

This type of autoepidermalgrafting technique is markedly different from conventional autografting techniques in numerous respects, which include the following:

1. Conventional autografting requires that a relatively thick layer of epidermis and dermis be harvested from a donor site. For example, the depth setting on a dermatome during a conventional harvesting operation usually ranges from about 0.010 to about 0.020 inch (0.25 to 0.5 mm). This increases the pain and the blood loss by the patient during the harvesting operation, and it usually leads to permanent scarring of the donor site. By contrast, the dermatome depth setting during an autografting technique using the bilayer membrane may be about 0.002 to 0.004 inch (0.05 to 0.1 mm). This removes a very thin layer of epidermis; the wound is approximately equal to a severe sunburn. It reduces the pain caused by the operation, and reduces or prevents blood loss by the patient and permanent scarring of the donor site.

2. Results of grafting operations by the Applicants on test animals and human burn victims indicate that autografts using the bilayer membrane promote the creation of regenerated skin that is substantially smoother, softer, more flexible, and less fibrotic than skin regenerated by using conventional autografts. All of these results are extremely desirable, and markedly improve the recovery, appearance, and functioning of a wounded area.

3. Autografting techniques involving severely burned patients often utilize xenografts or allografts to protect a wound until an autograft donor site is available. Xenografts and allografts provoke inflammation and an immune response, and are rejected by the patient's body. They act solely as temporary protective covering, and when they are removed they leave nothing behind. If immunosuppressive drugs are used to extend their useful period, the patient is rendered more vulnerable to infection. By contrast, the bilayer membrane, if properly prepared, does not provoke inflammation or rejection. This eliminates or reduces the need to use immunosuppressive drugs. When the silicone layer is removed, the collagen/GAG lattice remains attached to the woundbed, providing a biocompatible framework in which cells and blood vessels have grown and proliferated, and providing a suitable surface for the growth of epidermal cells.

4. Xenografts and allografts often suffer from dehydration, contraction and wrinkling, causing the patient discomfort and exposing the edges of the wound to possible infection. By contrast, the bilayer membrane, if properly prepared, does not suffer dehydration, contraction or wrinkling.

5. The bilayer membrane prevents, delays or reduces a wound contraction and the resultant scarring.

PREPARATION OF AN AQUEOUS SUSPENSION OF CELLS

Several preferred embodiments of this invention utilize one or more known techniques for dissociating a cohesive piece of skin into a suspension of living, reproducing cells in a liquid solution [9]. One common technique involves treating a piece of harvested skin with trypsin, collagenase, or other enzymes that cause cells to become detached from other cells or from solid surfaces. After a piece of skin is treated with one or more enzymes, a layer of epidermis is removed and discarded. The remaining tissue, which contains basal cells that reproduce at relatively high rates, is agitated with enough force to separate the cells without damaging them. For example, stirring at low speeds, vortexing, pipetting, and other forms of mixing can be used for this purpose. The cells are usually suspended in an aqueous solution that contains various salts that resemble the substances found in body fluids; this type of solution is often called physiological saline. It may be buffered by phosphate or other non-toxic substances, in order to maintain the pH at approximately physiological levels, and it may be supplemented by animal or human blood serum or other sources of protein or other nutrition. The density of the liquid may be controlled so that it is less than the density of the cells.

An important advantage of utilizing an aqueous suspension of cells is that it can be used to greatly expand the area or volume of a wound that can be closed quickly by multiplication of a limited number of cells. This provides for two distinct advantages. First, if a very limited amount of intact tissue is available for autografting, then the various suspension methods may be used to dramatically increase the area or volume of a collagen lattice that may be seeded with the limited number of available cells. Second, if a given area or volume of a collagen lattice needs to be seeded with cells, then the amount of intact tissue that needs to be harvested from a donor site may be greatly reduced. The optimal seeding densities for specific applications may be determined through routine experimentation by persons skilled in the art.

The number and concentration of cells seeded into or onto a collagen lattice can be varied by modifying the concentration of cells in suspension, or by modifying the quantity of suspension that is distributed onto a given area of volume of collagen lattice.

CENTRIFUGATION

One preferred embodiment of this invention comprises the use of centrifugal force to embed autologous cells into the collagen lattice before the membrane is grafted onto a patient. That method, which has been coinvented by I. V. Yannas, J. F. Burke, D. P. Orgill, and E. Skrabut, is the subject of a separate patent application U.S. application Ser. No. 315,234, filed simultaneously with this application, the teachings of which are hereby incorporated by reference.

METHODS FOR SEEDING AQUEOUS CELLULAR SUSPENSIONS

A liquid suspension containing autologous cells may be manually distributed onto a collagen lattice by any of several techniques, which include spreading, spraying, painting, and pipetting. A sequence of steps that may be used in these techniques is displayed as a flowchart in FIG. 4.

Figure 1:
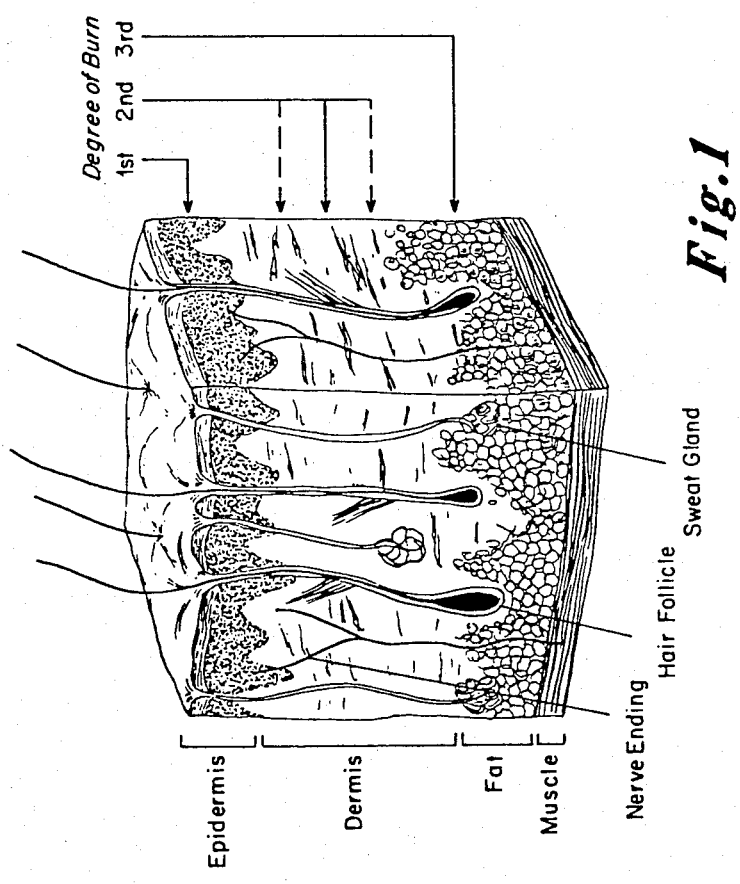
FIG. 1 is a simplified perspective view of a segment of skin.
Figure 2:
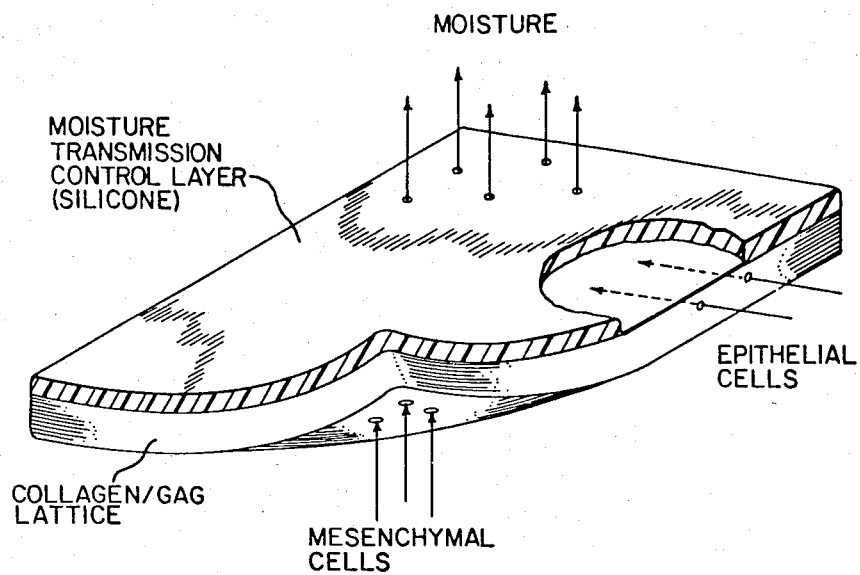
FIG. 2 is a perspective view of a bilayer membrane described in U.S. Pat. No. 4,060,081, suitable for cell seeding by the methods of this invention.
Figure 5:
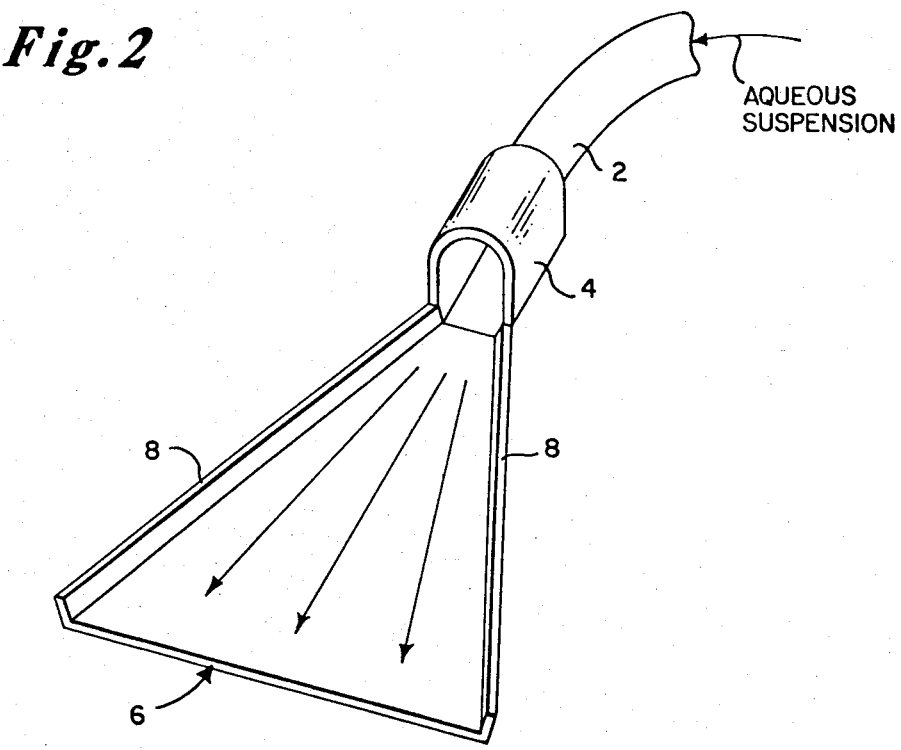
FIG. 5 is a perspective view of a device that can be used to spread an aqueous suspension of cells across a collagen lattice, according to this invention.

After eschar has been surgically removed if present from a skin wound, a piece of bilayer membrane is trimmed if necessary and sutured to the wound. Within several days, mesenchymal cells and blood vessels grow vertically from the woundbed into the collagen/GAG lattice. When a sufficient number of mesenchymal cells and blood vessels are present in the collagen lattice to enhance the growth of epithelial cells, a thin layer of intact skin is harvested from a donor site on the patient. Such skin may be harvested from an area that is substantially smaller than the wound area to be closed. The skin is treated by the methods mentioned above to create a suspension of living epithelial cells in aqueous solution. A piece of the silicone layer is removed from an area of the membrane by making an incision through the silicone and carefully peeling the silicone layer away from the collagen/GAG lattice. The epithelial cells in solution are then seeded randomly on the exposed collagen lattice by any of the following methods:

1. Spreading: This embodiment utilizes a spreading device such as the device shown in FIG. 5. Aqueous cellular suspension enters the device through tube 2, which is connected by conventional means to fitting 4. The suspension passes through fitting 4 onto flat plate 6, which is approximately triangular in shape. The suspension is retained on plate 6 by retaining edges 8. As it flow across plate 6, the suspension tends to disperse into a broad, shallow stream which crosses the lower edge of plate 6 and is distributed in a relatively even manner across the exposed collagen/GAG lattice. The liquid may be further distributed across the lattice by using plate 6 as a spatula.

The spreading device may be fabricated from any conventional material, such as plastic or metal. It may be coated with a substance such as silicone to control the flow of liquid across the surface of the device, and to reduce the affinity or adhesion between the suspension and the device. Fitting 4 may be equipped with a valve to control the flow of suspension through the device.

2. Spraying. The suspension may be sprayed through any type of nozzle that transforms liquid into small airborne droplets. This embodiment is subject to two constraints. First, it must not subject the cells in solution to shearing forces or pressures that would damage or kill substantial numbers of cells. Second, it should not require that the cellular suspension be mixed with a propellant fluid that is toxic or detrimental to cells or woundbeds. A variety of nozzles that are commonly available satisfy both constraints. Such nozzles may be connected in any conventional way to a reservoir that contains a cellular suspension.

3. Painting. An aqueous suspension of cells may be distributed across a collagen lattice by dipping a brush into the suspension, withdrawing it, and wiping the suspension-laden brush on the lattice. This method suffers the disadvantage that substantial numbers of cells may cling to the brush, and not be applied to the lattice. However, it may nevertheless be useful, especially in situations where it is desired to carefully control the pattern or area of lattice over which the suspension is distributed.

4. Pipetting. This embodiment comprises the use of pipettes, common "eye-droppers," and other similar devices to place small quantities of cellular suspension on a collagen lattice. The aqueous liquid will permeate through the porous lattice. The cells in suspension tend to become enmeshed in the fibers of the lattice, and are thereby retained upon or within the lattice.

5. Syringe Emplacement. In one preferred embodiment of this invention, an aqueous suspension of cells may be seeded into a porous collagen lattice by means of a hypodermic syringe equipped with a hollow needle or other conduit. A suspension of cells is administered into the cylinder of the syringe, and the needle is inserted into the collagen lattice. The plunger of the syringe is depressed to eject a quantity of solution out of the cylinder, through the needle, and into the lattice.

One advantage of syringe emplacement is that it can be used to penetrate without removing a heterogenous covering that surrounds a collagen lattice, such as the moisture transmission control layer of the multilayer membrane described in U.S. Pat. No. 4,060,081. Heterogenous coverings may also be useful to impart shape, strength, fluid integrity, or other desired properties to collagen lattices used for other purposes, such as organ prosthetics.

When the cell distribution process is complete, the seeded lattice is covered and protected by a bandage.

ALTERNATE MODES OF CARRYING OUT THE INVENTION

Cells can be seeded by the methods of this invention into a porous lattice of virtually any chemical composition. Although the collagen/GAG lattices disclosed in U.S. Pat. Nos. 4,060,081 (Yannas et al, 1977) and 4,280,954 (Yannas et al, 1981) contain a relatively small weight percentage of glycosaminoglycan (GAG) to improve the biocompatibility and physical properties of the collagen, the presence of GAG or any other substance within a collagen lattice is not necessary for the purpose of this invention.

Although the research that led to this invention involved collagen, the cell seeding methods of this invention are not limited to methods for seeding collagen. Subsequent research may reveal that other fibrous proteins, other polymeric molecules, or sintered ceramics may also be suitable for prosthetic or other medical purposes. If such other molecules are formed into porous lattices that are seeded by the methods of this invention, then such seeding processes, and such seeded lattices, are within the scope of this invention.

The term "lattice" is used broadly herein to include any material which is in the form of a highly porous and permeable structure in which cells can migrate and proliferate.

"Fibrous lattices" should be construed broadly to include all lattices which include material that is fibrous at the macroscopic, microscopic, or molecular level. For example, many polymeric foams comprise long organic molecules, which may have numerous side chains or extensive crosslinking. Alternatively, sintered ceramic materials comprise numerous particles which may be regarded as fibrous in shape or nature. Any such material, if formed as a lattice that is seeded with cells by the methods of this invention, is within the scope of this invention.

It is possible to seed cells into lattices of any shape or configuration. For example, it may be possible to create molded bilayer membranes in the shape of a face, a hand, or another irregular surface. Such lattices may be seeded with cells by the methods of this invention, and are within the scope of this invention.

The various methods of this invention may be used in combination with each other. For example, when a burn patient is first admitted to a hospital, autologous cells may be harvested from the patient, dissociated into an aqueous suspension, and centrifugally seeded into a bilayer membrane that is grafted onto the patient during the initial operation. If an insufficient number of healthy epithelial cells is available, or if some of the centrifuged cells fail to generate colonies for any reason, then areas of the would might not be closed by neoepidermis generated from the centrifugally seeded cells. Areas of unclosed wound can be identifed by visually monitoring the transparent silicone layer of the membrane. These areas can be reseeded by one or more of the other embodiments of this invention. For example, large voids in the epithelial coverage may be seeded by removing an area of the silicone layer and spraying or spreading a quantity of a suspension of cells onto the exposed collagen lattice. Small gaps in the epithelial coverage may be seeded by syringe emplacement of cellular suspension.

Fibrous lattices may support the growth of many types of cells, including cells from numerous organs of the body, from bones, and from contractile or connective tissue. A fibrous prosthetic used to replace an organ or bone that is fully or partially removed from the body may be many centimeters thick in all directions. The use of syringe emplacement or centrifugal force may be very useful to seed cells into the interior of thick prostheses. In addition, it is possible to permeate a suspension of cells through a porous lattice, which will retain cells by an effect similar to filtration.

Autologous cells, as described previously herein, were restricted to cells taken from the patient, or from the patient's identical twin. This is a reflection of the current status of grafting techniques. Using the current techniques, non-autologous cells tend to be rejected by a wound. However, subsequent advances in cell typing and matching, cell treating to remove or inactivate surface or secreted antigens or other molecules, immunosuppressive agents, and other techniques may reduce or eliminate this problem, thereby rendering non-autologous cells suitable to reconstitute lost tissue, bone, or organ. Any such cells which are matched or treated in such a manner would be suitable for seeding into a fibrous lattice by the methods of this invention. Such cells are within the scope of this invention.

Various types of fibrous lattices may be suitable for use as temporary prosthetic devices within most regions of the body, including skin, blood vessels, bones, connective tissue, contractile tissue, and organs. Such lattices provide a structural system in which virtually any type of cell may grow, migrate, and proliferate. They can be surgically emplaced within virtually any region of the body, and if properly seeded with the appropriate type(s) of cells, may allow for the regeneration of new tissue. For example, if a patient suffers damage to or disease of an organ, a portion of the organ may need to be removed. A fibrous lattice may be emplaced in the location created by removal of part of the organ. If a sufficient number of healthy cells from another part of that organ, or from a compatible donor, is seeded into the lattice by the methods of this invention, it may be possible to greatly promote the recovery and regeneration of the organ. Such use falls within the scope of this invention.

It is possible to preserve harvested tissue or cells in suspension for a period of days in relatively cold (e.g., 4° C.) aqueous solutions. This allows the option of harvesting tissue from a donor site at a preferred time. For example, healthy epidermis may be harvested during an admittance operation while eschar is being removed from a wound or while a collagen/GAG membrane is being grafted onto a wound. In either situation, the patient is likely to be under general anesthesia. The harvested epidermis may be preserved, and applied to the collagen lattice after sufficient mesenchymal cells and blood vessels have grown into the collagen lattice to enhance epithelial proliferation.

It is also possible to culture cells in vitro after they have been harvested, before they are seeded into a collagen lattice. This would allow for several distinct advantages. For example, it can be used to increase the number of cells that are available for seeding, thereby reducing the amount of tissue that must be harvested to cover a wound. In addition, this allows for the use of cell "banks." For example, people who work in high-risk occupations could donate cells that can be cultured in vitro and available for seeding into a fibrous lattice if an accident or injury occurs. The seeding of preserved or cultured cells into fibrous lattices by the methods disclosed herein are within the scope of this invention. Cell banks and tissue cultures from which cells of a desired variety are taken for seeding are within the term "donor sites" for the purposes of this invention.

A variety of techniques are known for contacting cells with various substances that increase the reproductive rate of certain types of cells. For example, it is known that epidermanl growth factor [10], fibronectin [11], cyclic nucleotides [12], choleratoxin [13], platelet derived growth factor [14], tissue angiogenesis factor [15], and various other substances [16] are capable of increasing the rate of proliferation and/or surface adherence of one or more types of cells. Prior to seeding cells into a collagen lattice by the methods of this invention, it is possible to contact such cells with any substance that is known or hereafter discovered to increase the rate of reproduction of such cells. Such pre-seeding treatment may be used to increase the number of cells that are available for seeding, or to induce the cells to reproduce more rapidly after they have been seeded. Such pre-seeding treatment or neodermal surface treatment is within the scope of this invention.

CHARACTERISTICS OF SEEDED COLLAGEN LATTICES

The invention described herein comprises several methods of seeding cells into or onto fibrous lattices. It also comprises a composition of matter which is a fibrous lattice that is seeded with cells by the methods of this invention. In order to further define that composition of matter, the following information is provided regarding a collagen lattice that is further described in U.S. Pat. Nos. 4,060,081 (Yannas et al, 1977) and 4,280,954 (Yannas et al, 1981 ), the teachings of which have previously been incorporated by reference.

The physiological response of a wound to a grafted collagen lattice depends upon a combination of characteristics of the lattice, rather than upon any single characteristic acting as an isolated factor. Therefore, it is preferable not to specify an optimal numerical value of any single characteristic. Instead, a range of values can be specified for most characteristics, which assumes that all other characteristics are simultaneously within suitable ranges. It must also be noted that the correlations mentioned between parameters and characteristics are not exhaustive; instead, only the most direct correlations are mentioned.

1. Controllable Biodegradation. A collagen lattice, when in biochemical communication with a wound surface, eventually is biodegraded by collagenase and other natural enzymes into non-toxic substances that are digested, utilized, or eliminated by normal bodily processes. The lattice must retain its structural integrity until an adequate number of cells have reproduced within the lattice to regenerate the lost or removed tissue. If the lattice is biodegraded more quickly than this, it will be liquified and rendered useless before the wound has healed. On the other hand, research by the Applicants indicates that if the lattice is biodegraded too slowly, it tends to promote the formation of a dense fibrotic sac surrounding the lattice. This sac impedes the healing of the wound and tends to exacerbate scarring.

Research with the bilayer membrane indicates that the ideal biodegradation rate should be roughly equal to approximately 25 to 30 days. This does not mean that the entire lattice should be biodegraded within 30 days. Instead, it indicates that a significant amoung of biodegradation should commence within about 30 days, although remnants of the lattice may persist for several months or more. Routine experimentation by persons skilled in the art might indicate that this biodegradation rate should be modified somewhat for lattices that are seeded with cells, or for lattices that are used for purposes other than synthetic skin.

The biodegradation rate of a collagen lattice may be decreased (i.e., the lattice will endure for a longer period of time after grafting onto a wound) by increasing the collagen crosslinking density, by increasing the content of GAG that is crosslinked with collagen, or by decreasing the porosity of the lattice.

The silicone layer of the bilayer membrane is not biodegradable. However, this is satisfactory and even preferable, since this layer is spontaneously ejected (without requiring surgical invasion or removal) after neoepidermal tissue has been regenerated below it.

2. Non-antigenic and non-inflammatory. Xenografts, allografts, and transplanted organs normally contain cells that are recognized as foreign by the immune system of the patient. In a typical immune response, antibodies and certain types of cells such as lymphocytes identify and take part in the attack on foreign cells unless immunosuppressive drugs are used to suppress the formation of antibodies or defensive cells. However, the use of such drugs renders the patient more vulnerable to infection. The use of such drugs can be rendered unnecessary if the grafted substance does not have antigenic or inflammatory properties.

The collagen/GAG lattice that has been coinvented by the Applicants may be manufactured so that it does not possess antigenic or inflammatory properties, by adjusting the chemical content and crosslinked structural arrangement of the collagen and GAG molecules. If properly prepared, it is readily accepted by wound surfaces without provoking rejection by the patient.

3. Affinity for a Wound Surface. A collagen lattice must possess sufficient affinity for a wound surface to efficiently wet the surface and maintain contact with it. This affinity is usually expressed as surface tension or surface energy of an interface, measured in terms of force per area. The surface energy of an interface between a wound and a collagen lattice should be lower than the surface energy of an interface between the wound and the atmosphere. This criterion is satisfied by the collagen/GAG lattice coinvented by the Applicants.

4. Tensile Strength. A synthetic membrane or prosthetic device should be sufficiently tough and strong to withstand suturing without tearing, and to prevent or limit tearing if subjected to accidental stresses caused by bandaging or medical operations or by patient movement. The two most important indices of strength of a lattice are tensile strength (which measures how much force is required to pull apart a specimen with a known cross-sectional area) and fracture energy (which measures how much work is required to create a tear of a given size). The collagen/GAG membrane has a tensile strength range of approximately 50 to 1,000 psi, and a fracture energy that ranges from approximately $1 \times 10^5$ to about $5 \times 10^6$ ergs/cm$^3$. The strength of the lattice may be increased by increasing the crosslinking density or by decreasing the porosity of the lattice.

5. Morphology. In general, "morphology" relates to the size and spatial arrangement of the fibers within a lattice. As such, it may be regarded as the converse of "porosity," which relates to the size, shape, and spatial arrangement of the open spaces between the fibers within a lattice.

A synthetic collagen lattice that serves as a prosthetic device should resemble the collagen matrix that exists naturally within the type of tissue that is to be regenerated. This spatial arrangement will promote the growth of cells in orderly patterns that resemble undamaged tissue, thereby reducing scarring and promoting proper functioning of the regenerated tissue.

Significant morphological characteristics of a porous collagen lattice include:

a. Volume fraction of the fibers, which is equal to the volume occupied by the fibers, divided by the total volume of the lattice. This fraction is the converse of porosity, which is discussed below.

b. Mean aspect ratio, which is the ratio of the average length of the fibers to the average width. A lattice composed of long and thin fibers would have a high mean aspect ratio.

c. Mean orientation of fiber axes, which indicates whether the fibers are randomly oriented in all directions, or whether substantial numbers of fibers are oriented in roughly parallel directions along one or more axes within the lattice.

d. Mean distance between fiber axes, which indicates how far apart adjacent fibers are. This characteristic is directly related to pore size.

It is believed that the porous collagen/GAG lattice that has been coinvented by the Applicants has morphological characteristics that resemble the collagen matrixes that exist normally in mammalian dermis. Therefore, the aforementioned lattice is very suitable as a prosthetic device to promote the regeneration of lost or damaged skin. Research may indicate that other types of tissue also have similar morphological characteristics, and thus may be well-suited to regeneration by the collagen/GAG lattice described above. In addition, research may indicate methods of altering the morphological characteristics of collagen lattices to resemble the collagen matrixes that exist in other types of tissue. Such lattices, if seeded with cells by the methods of this invention, are within the scope of this invention.

6. Porosity. Four interrelated aspects of porosity affect the rate of cell migration and reproduction within a collagen lattice:

a. Porosity, also called pore fraction, which is a fraction that is equal to the volume of the lattice. This fraction may be multiplied by 100 to convert it to a percentage. High porosity is desirable, because it provides more space in which cells can grow and multiple. Porosity may be modified to control the rate of biodegradation and the flexural rigidity of a collagen lattice.

Research involving the bilayer membrane indicates that porosity of at least about ninety percent is desirable to encourage cell migration and reproduction within or on the surface of the lattice. Additional research by the Applicants indicates that if porosity is at least about ninety-five percent, epithelial cells tend to migrate between the collagen/GAG lattice and the top silicone layer of the membrane. This is very desirable, since it allows the silicone layer to be spontaneously ejected when neoepidermal skin is regenerated beneath it.

b. Pore shape and distribution, which relates to the shape of the pores and the orientation of the fibers.

c. Pore size, which indicates the diameter of the average or mean pore. The pores within a collagen lattice must be large enough for cells to grow in and migrate through. Research by the Applicants indicates that average pore sizes of approximately 50 μm tend to encourage satisfactory cell migration and reproduction. Routine experimentation by those skilled in the art may indicate that average size, and possibly the distribution of pore size about the average, should be varied to enhance cell migration and reproduction for various uses of collagen lattices.

d. Connectivity, also called permeability, whether the pores are isolated or interconnected. A closed-cell foam does not allow fluid or other material to move through it; each bubble is trapped. This type of lattice would be unsuitable for cell migration. By contrast, a permeable lattice contains pores that are interconnected; this allows the movement of fluids or cells between pores. The fibrous nature of collagen, and the freeze-drying procedures that is used to create the lattices that are used in this invention, ensure that the lattices are sufficiently permeable to permit cell migration.

7. Reduction of Wound Contraction. Wound contraction normally involves migration of cells in and on the periphery of a wound. For example, if a small piece of skin is lost or removed from an animal or human, the surrounding skin will tend to move across the fascia to close the wound. This results in distortion and scarring of the wounded area, and it is very detrimental to accurate return to normal function. Research by the Applicants indicates that proper creation and emplacement of the bilayer membrane tends to delay and reduce wound contraction, which reduces scarring and contracture deformity and promotes the regeneration and proper functioning of neoepidermal skin.

8. Flexural Rigidity. When placed in contact with a wound surface, a collagen lattice should be sufficiently flexible to prevent pockets of air from being trapped between the woundbed and the lattice. Such pockets of entrapped air, often called dead space, become filled with fluid and often develop into sites of bacterial proliferation and infection, and therefore should be avoided. Efficient wetting requires the use of a lattice with relatively low rigidity.

Flexural rigidity is a function of the shape of the lattice and the modulus of elasticity of the material. The rigidity of a membrane used as artificial skin may be reduced by reducing the thickness of the membrane; however, an organ or bone prosthesis may be constrained to a specific shape. The modulus of elasticity (often called Young's modulus) must be sufficiently low to reduce the flexural rigidity of a collagen lattice to acceptable levels, but sufficiently high to withstand moderate compressive forces without buckling. Materials with a Young'e modulus between about 1 and about 100 psi (depending on the thickness and shape of the lattice) are preferred. The Young's modulus of a collagen lattice may be increased by decreasing the porosity or increasing the crosslinking density.

9. Moisture Flux. Moisture flux relates to the amount of water or other liquid that will permeate through a given area of a membrane during a given period of time, expressed by gm/cm$^2$/hr or similar terms.

If the moisture flux of a membrane used as synthetic skin is too high, too much fluid will leave the wound, and the woundbed and the membrane will dehydrate, causing shrinkage and curling of the membrane. On the other hand, if the moisture flux of the membrane is too low, fluid will accumulate beneath the membrane, disrupting the desired physiological processes. Such fluid accumulation is usually called exudate or edema. To avoid either extreme, the moisture flux of a membrane used as synthetic skin should approximate the moisture flux of normal skin.

The moisture flux of the collagen/GAG membrane may be easily controlled by modifying the thickness of the silicone layer. It has been found that a silicone layer of approximately 0.1 to 1.0 mm provides a moisture flux that is in the appropriate range.

EXAMPLES

Example 1: Preparation of Bilayer Membranes

Collagen from bovine hide, prepared by the methods described by M. Komanowsky et al, *J. Amer. Leather Chemists Assn.* 69: #9, p. 410–422 (1974), was donated by the Eastern Regional Research Center, U.S. Department of Agriculture, Philadelphia, PA. It was ground in a Wiley mill (A. H. Thomas Company, Philadelphia, PA) using a 20-mesh screen, cooled with liquid nitrogen. To prepare each membrane, 0.55 g (hydrated weight) of milled collagen was added to 200 ml of 0.05 M aqueous acetic acid. This solution was stirred for 60 minutes in an iced-jacketed blender (Eberbach Corp., Ann Arbor, MI) on a 2-speed power unit (Waring Company, Hartford, CT) set on high speed with the line voltage reduced to 60 volts.

0.044 g of chrondroitin 6-sulfate (hydrayted weight) obtained from shark cartliage (sodium salt form, type C, Sigma Chemical, St. Louis, MO) was dissolved in 40 ml of 0.05 M acetic acid. Over a period of five minutes, the C6S solution was added to the collagen dispersion during blending. The mixture was blended for an additional 10 minutes, then centrifuged at 1500 g for one hour in a refrigerated centrifuge (Model CRU-5000, International Equipment, Needham Heights, MA) maintained at 4° C. The dispersion was removed from the centrifuge, and 140 ml of supernatant was decanted for each 240 ml of the dispersion which was centrifuged. The concentrated dispersion was then blended for 15 minutes in the Eberbach blender at high speed setting, 60 volts. The dispersion was then poured into freezing trays; 2 ml of dispersion were applied to each square inch of tray surface. The trays were placed on a precooled freezing shelf maintained at −45° C. (Model 10-MR-PC, Virtis Company, Gardner, NY). The trays were allowed to freeze and equilibrate with the shelf temperature for about one hour. The pressure in the chamber was then reduced to less than 100 mtorr, and the trays were allowed to stand for an hour. The shelf temperature was increased to 0° C. The samples were lyophilized for a period of 24 to 48 hours.

The resulting foams were removed, wrapped in aluminum foil, and placed in a vacuum oven maintained at 105° C. and 50 mtorr for a period of about 24 hours. After removal from the oven, the foams were either stored in a dessicator, or cooled and coated with silicone adhesive.

Silicone adhesive (medical grade, Dow Silastic catalog #891, Dow Chemical Company, Midland, MI) was coated over the entire surface of the cooled foam. The silicone was coated over the foam surface that was not in contact with the freezing tray. The silicone was applied with a spatula to a thickness of approximately 0.1 to 0.5 mm. The bilayer membrane was placed silicone side down in 0.05 M acetic acid at room temperature for 24 hours to allow the silicone to cure. The membrane was then turned silicone side up and allowed to rehydrate in 0.05 M acetic acid for 24 hours at room temperature. The acetic acid was removed and replaced with 0.05 M acetic acid which contained 0.25% by volume glutaraldehyde (practical grade, catalog #8-752, J. T. Baker Chemical Co., Phillipsburg, NJ). The glutaraldehyde cross-linking treatment lasted for 24 hours at room temperature. The glutaraldehyde solution was removed, and the material was rinsed twice in distilled, deionized water. The foam was stored in water for 24 hours at room temperature, then transferred to a storage container. It was stored in a solution of 70% isopropanol in water at 4° C. until shortly before use.

Typical characteristics of membranes prepared by those methods are indicated in Table 1.

TABLE 1

Characteristics of Bilayer Membranes
Prepared as Described in Example 1

| Tensile strength | |
|---|---|
| C/GAG lattice | 2 to 5 × $10^4$ newtons/$m^2$ |
| Bilayer membrane | 7 to 10 × $10^4$ newtons/$m^2$ |
| Average pore diameter | |
| C/GAG lattice before wetting | 80 microns |
| Average porosity | |
| C/GAG lattice before wetting | 96% |
| Moisture flux | |
| Bilayer membrane | 1 to 10 mg/$cm^2$/hr |
| Bending rigidity of 1 cm wide strip | |
| C/GAG lattice | 5 to 150 × $10^{-9}$ newton-$m^2$ |
| Bilayer membrane | 10 to 500 × $10^{-9}$ newton-$m^2$ |
| Antigenicity | Very low |
| Pyrogenicity | Not detectable |
| Significant biodegradation | 25 to 30 days |
| Mean orientation of fiber axes | Random |

Example 2: Autografting Procedures on Humans

Ten patients, ranging in age from 3 to 60 years, suffering third-degree burns over 50% to 90% of their body surface area (BSA) were treated using bilayer membranes prepared as described in Example 1. Six patients were treated at the Massachusetts General Hospital and four patients were treated at the Shriner's Burn Institute in Boston.

All patients were treated with prompt excision of eschar, which was carried out in stages if necessary. Each excisional operation was limited to 15 to 20% BSA. In each operation, the wound was closed by meshed autograft that had been harvested during the same operation. After all available autograft had been used, excised wounds were closed with the bilayer membrane immediately following excision. The bilayer membrane was supplied in sheets measuring 4×6 inches. It was tailored to fit the existing wound and sutured in place using interrupted sutures of 5-0 chromic catgut. Great care was taken in constructing the suture lines between unburned skin and the membrane to achieve primary closure. The membrane was sutured under slight tension to prevent wrinkling. If wrinkles developed during the post-operative period, the ridge of the wrinkle was debrided and serous fluid which collected underneath was drained. Most membranes were dressed using a quilting technique, wherein numerous stitches extended into the deep fascia to reduce shearing motion between the membrane and the woundbed.

The collagen/GAG lattice served as a template to support infiltration of mesenchyman cells (including fibroblast cells and blood vessels) to synthesize a neodermis. Vascularization of the lattice was evident by blanching when finger pressure was applied after three to five days.

When autograft donor sites were suitable for reharvesting, the patient was returned to the operating room and donor sites were reharvested with a dermatome set of 0.004 inches depth. This obtained a very thin graft containing primarily of epidermis with small irregular patches of dermis. The silicone layer was then peeled from the collagen/GAG lattice. Capillary bleeding was controlled using saline packs. The collagen/GAG lattice was then covered with the epidermal autograft; both sheet and three-to-one meshed grafts were used. The grafts were sutured and dressed using conventional techniques.

The results of these operations are displayed in Table 2. The reconstituted skin that was regenerated with the assistance of bilayer membrane was smoother, more uniform, less fibrotic, less scarred, and more flexible than tissue that was regenerated by wound contraction or by conventional autografting.

In wounds that were treated with meshed autografts applied to collagen/GAG lattices, interstitial tissue growth proceeded at the rate expected from conventionally harvested and meshed autografts which contain not only epidermis but substantial dermis. However, autografts utilizing the bilayer membrane exhibited very little evidence of a meshing pattern after early epidermal closure. After several months the mesh pattern could be detected only on very careful observation. In addition, harvesting of very thin layers of epidermis allowed for prompt recovery of the donor sites, usually within a week after harvesting, even in areas which had been harvested repeatedly.

TABLE 2

Characteristics of Artifical Skin Grafts
Using Autograft Embodiment

| | |
|---|---|
| Number of Patients | 7 males and 3 females |
| Type of Burn | Flame |
| Total Burn Size | 50 to 95% BSA (average 77%) |
| Third-Degree Burn Size | 50–90% BSA (average 64%) |
| Total Area Covered With Artifical Skin | 15–60% BSA (average 27%) |
| "Take" of Bilayer Membrane on Woundbed | 95–100% |
| "Take" Autograft on Collagen/GAG Material | 85–95% |
| Membrane Loss Secondary to Infection | None |
| Membrane Loss Secondary to Hematoma | 3% BSA of 1 patient |
| Long Term Clinical, Cosmetic, and Functional Results | Good to excellent |

Example 3: Preparation of Aqueous Cellular Suspensions

In order to use several of the various embodiments of this invention, it is necessary to prepare an aqueous suspension of autologous cells. Such cells may be harvested from a guinea pig back or from a human body using a dermatome, or from the rim of a guinea pig's ear.

Harvested skin is placed in cold (4° C.) phosphatebuffered saline solution (PBS) without calcium or magnesium (catalog #17-515B, M.A. Bioproducts, Walkersville, MD). Before the skin is treated with trypsin, it is transferred to warm PBS (about 30° C.). The skin is then incubated at 37° C. for 40 minutes in a solution of 2.5% trypsin in Hanks' balanced salt solution without calcium or magnesiium (catalog #17-160H, M.A. Bioproducts), diluted with PBS to 0.25% trypsin. Following incubation, the epidermal layer is separated from the dermal layer and discarded. The dermal layer, which contains a relatively high number of reproductive basal cells, is transferred to tissue culture medium (Dulbecco's modified eagle medium without glutamine, catalog #12-707B, M.A. Bioproducts, supplemented with 10% fetal calf serum and L-glutamine shortly before use). This solution is then vortexed for 1.5 minutes to release basal cells from the tissue. The suspension is then filtered through sterile gauze to remove large tissue fragments.

Cell concentration is determined by using a cell counting chamber or electronic particle counter. Cell viability is determined by staining an aliquot of cells with trypan blue (Grand Island Biological Company, Grant Island, NY). The cell density is adjusted to approximately $10^6$ viable cells/ml by addition of tissue culture medium.

Example 4: Procedures for Seeding Cellular Suspensions

Various methods of distributing aqueous cellular suspension into collagen/GAG lattices sutured to woundbeds have been used on a total of about 30 guines pigs and about 30 rats. In a typical operation, a segment of split or full-thickness animal skin, including epidermis and dermis down to the *panniculus carnosus,* is removed from an area of the animal's back. Most such excisions were 1.5×3.0 cm. The skin is surgically removed, and replaced by a segment of bilayer membrane created as described in Example 1. The membrane is tailored to fit the wound, and sutured into place under slight tension using conventional techniques.

Figure 4:
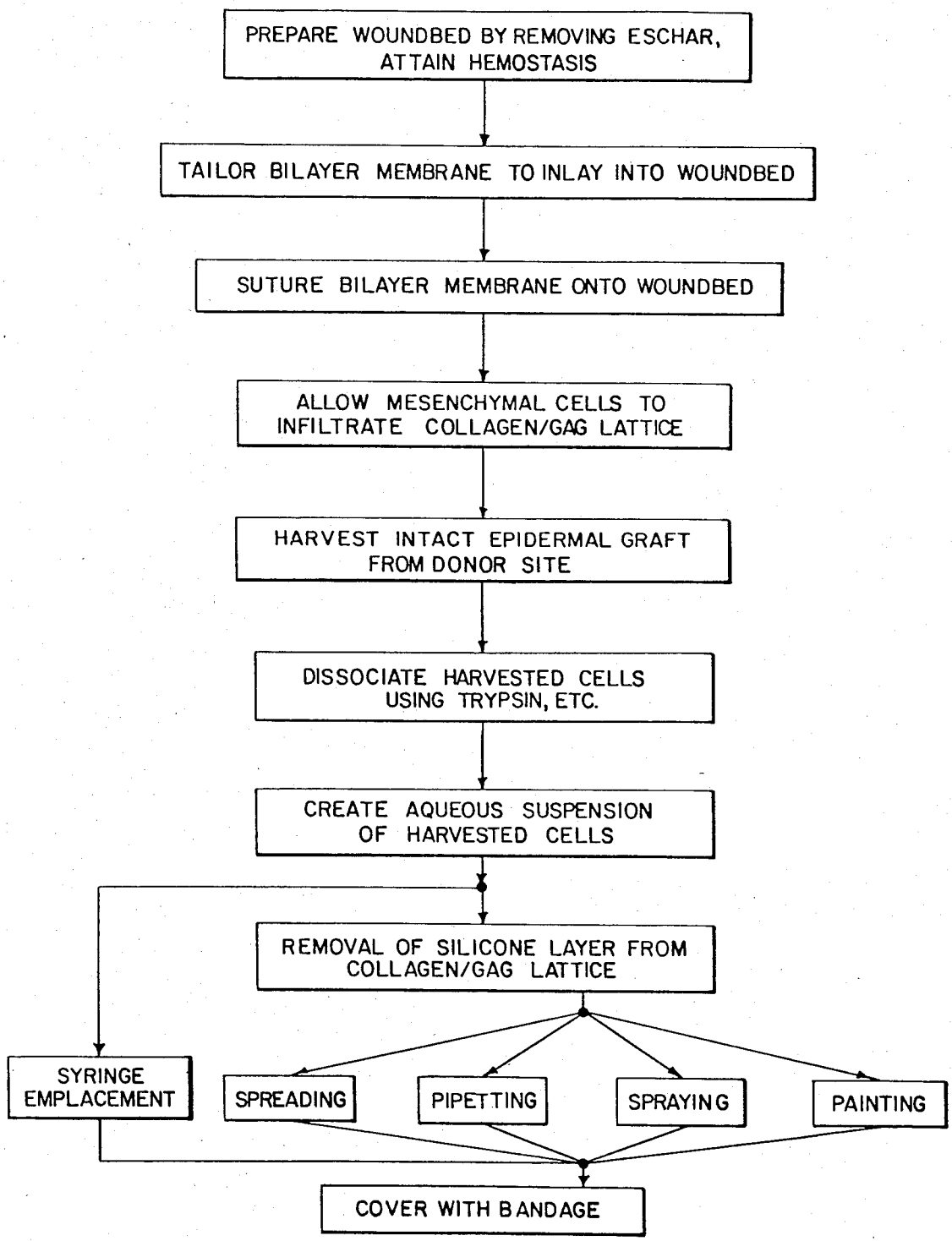
FIG. 4 is a flow chart indicating a sequence of steps comprising embodiments that may be used to distribute aqueous cellular suspension upon a collagen lattice according to this invention.

Visual monitoring indicated that the collagen/GAG lattices became vascularized within a period of approximately 5 to 7 days. After a period ranging from 7 to 10 days, the silicone layer was carefully peeled off of the woundbed, exposing an area of vascularized collagen/GAG lattice. An aqueous suspension of autologous cells, prepared as described in Example 3, was administered to the exposed lattice by any of the following techniques:

a. spreading a quantity of suspension across the lattice by means of a silicone-coated plastic device as shown in FIG. 4;

b. spraying a quantity of suspension across the lattice by means of a spring-loaded device mounted on a small bottle;

c. pipetting a quantity of suspension onto the lattice, and allowing the liquid to permeate into the lattice;

d. using a hypodermic syringe to inject a quantity of suspension through the moisture control layer and into the collagen/GAG lattice.

All of the foregoing techniques were successful in emplacing epithelial cells that reproduced into colonies of cells. Most of the animals were sacrificed for histological studies before the cell colonies fully closed the wounds. However, on those animals that were not sacrificed before wound closure, the cell colonies grew to confluence and created a permanent, functional layer of neoepidermis. Although the neoepidermal areas tended to lack hair follicles, sebaceous glands, or sweat glands, the neoepidermal layers were smoother, less scarred, and less fibrotic than neoepidermis generated by wound contraction or unaided healing. Wound closure aided by a properly seeded collagen/GAG lattice usually occurred within about 10 to 14 days.

INDUSTRIAL APPLICABILITY

This invention has industrial applicability in the use of fibrous proteinous lattices to promote the growth of cells and tissue.

EQUIVALENTS

Those skilled in the art will recognize, or be able to ascertain using no more than routine experimentation, numerous equivalents to the specific procedures and seeded lattices described herein. Such equivalents are considered to be within the scope of this invention, and are covered by the following claims.

REFERENCES

1. See, e.g., R. H. Sims et al, *An Introduction to the Biology of the Skin* (F. A. Davis Co., Phila., 1970); W. Montagna et al, *The Structure and Function of Skin*, 3rd edition (Academic Press, New York, 1974); H. Gray, *Anatomy, Descriptive and Surgical*, 15th edition, p. 1135 et seq. (Bounty Books, New York, 1977). 2. See, e.g., H. C. Polk Jr. et al, editors, *Contemporary Burn Management*, p. 345 et seq. (Little, Brown & Co., Boston MA, 1971).

3. See, e.g., Polk et al, supra note 2, p. 412 et seq.

4. See, e.g., J. F. Burke et al, *Ann. Surg.* 182(3): p. 183-195 (1975).

5. See, e.g., Polk et al, supra note 2, p. 362 et seq.

6. See, e.g., Polk et al, supra note 2, p. 385 et seq.

7. See, e.g., Polk et al, supra note 2, p. 383 et seq.

8. See, e.g., R. Fleischmajer et al, *Epithelial-Mesenchymal Interaction* (Williams and Wilkins, Baltimore, 1968); R. H. Kahn et al, In Vitro 8: 451 (1973); R. H. Kahn et al, *J. Nat'l Cancer Inst.* 53: 1471 (1974); M. Regnier, *Acta Dermatovener* (Stockholm) 53:241 et seq. (1973); Rheinwald et al, Cell 6:317 (1975).

9. See, e.g., M. Prunieras, *J. Investigative Dermatology* 67: p. 58 et seq. (Williams & Wilkins, Baltimore, 1976).

10. See, e.g., R. O. Grepp, *Recent Progress in Hormone Research* 30:533 et seq. (Academic Press, New York, 1974); R. H. Starkey et al, *Science* 189:800 (1975).

11. See, e.g., L. B. Chen et al, *Science* 197:776 (1977).

12. See, e.g., D. M. Prescott, editor, *Reproduction of Eurkaryotic Cells*, p. 107 et seq. (Academic Press, New York, 1976).

13. See, e.g., A. W. Bernheimer, editor, *Mechanisms in Bacterial Toxicology* p. 53-84 (Wiley, New York, 1976); D. M. Gill, *Adv. Cyclic Nucl. Res.* 8: 85 et seq. (1977).

14. See H. N. Antoniades et al, *Proc. Natl. Acad. Sci.* 76: 1809-1813 (1979).

15. See J. Folkman et al, *J. Exp. Med.* 133:275 (1971).

16. See, e.g., H. Green, *Cell* 15: 801,805 (1978).

We claim:

1. In the method of using a fibrous lattice which:
   a. has controllable biodegradability in the presence of body enzymes;
   b. provokes no substantial immune respone or inflammation when grafted or implanted into a wound;
   c. has sufficiently high porosity, pore size and permeability to allow cell migration and reproduction; and
   d. has sufficiently high strength to resist tearing and collapse if grafted onto a wound, the improvement comprising seeding cells into said lattice.

2. In the method of using a fibrous lattice which has morphological characteristics that substantially resemble the morphological characteristics of the intercellular proteinous matrix that normally exists within healthy tissue, the improvement comprising seeding cells into said lattice.

3. A method of claims 1 or 2 wherein said lattice comprises collagen molecules that are crosslinked and covalently bonded to glycosaminoglycan.

4. A method of claims 1 or 2 wherein, prior to seeding cells into said lattice, said cells are contacted with a substance that increases the rate of reproduction of said cells.

5. A method of claim 3 wherein said glycosaminoglycan is selected from the following group: chondroitin 6-sulfate, chondroitin 4-sulfate, heparin, heparan sulfate, keratan sulfate, dermatan sulfate, chitin, and chitosan.

* * * * *